United States Patent [19]
Parker et al.

[11] Patent Number: 4,709,579
[45] Date of Patent: Dec. 1, 1987

[54] MEASUREMENT OF MOISTURE CONTENT

[75] Inventors: Merle A. Parker; Richard A. Pregnall; Hassan J. Ahmed, all of Columbia, S.C.

[73] Assignee: Westinghouse Electric Corp., Pittsburgh, Pa.

[21] Appl. No.: 766,306

[22] Filed: Aug. 16, 1985

[51] Int. Cl.$^4$ .............................................. G01N 5/02
[52] U.S. Cl. ........................................ 73/76; 73/73; 376/245; 34/89
[58] Field of Search .................... 73/73, 75, 76; 34/89; 376/245, 251

[56] References Cited

U.S. PATENT DOCUMENTS

| | | | |
|---|---|---|---|
| 1,392,116 | 9/1921 | Chopin | 73/76 |
| 2,379,045 | 6/1945 | Sturgis | 73/76 |
| 2,828,623 | 4/1958 | Benedict | 73/76 |
| 2,843,169 | 7/1958 | Stein | 73/76 |
| 2,931,718 | 4/1960 | Greaves | 73/73 |
| 2,976,722 | 3/1961 | Heckly | 73/76 |
| 3,731,520 | 5/1973 | Hickman et al. | 73/73 |
| 3,940,313 | 2/1976 | Steven | 376/251 |
| 3,945,245 | 3/1976 | Stehle et al. | 73/40 |
| 4,221,058 | 9/1980 | Zagorzycki | 34/89 |
| 4,485,284 | 11/1984 | Pakulis | 73/73 |

FOREIGN PATENT DOCUMENTS

| | | | |
|---|---|---|---|
| 0073652 | 5/1982 | Japan | 73/73 |
| 1175142 | 12/1969 | United Kingdom | 73/76 |

Primary Examiner—Charles Frankfort
Assistant Examiner—Thomas B. Will

[57] ABSTRACT

Nuclear fuel rods are processed to remove moisture in an oven which is evacuated. Measurement of the moisture content in each of a plurality of nuclear fuel rods (typically 44) is carried out by condensing the vapor derived from one randomly-selected control rod in a nitrogen-liquid cooled trap, collecting the condensed vapor in magnesium perchlorate, and determining the weight of the collected moisture. Moisture from the one fuel rod is condensed, collected and has its weight determined repeatedly in increments until the difference between the weight of a last increment and of a just preceding increment is less than 1 mg. (The permissible content is 6 mg. or less.) The rods have small perforations through which the vapor can escape. The evacuating system includes a main evacuating channel connected directly to the oven and a branch channel connected to the one fuel rod through the cold trap. The temperature of, and the vacuum in, the one fuel rod is the same as for the other rods and the residual moisture content after processing must be the same.

12 Claims, 1 Drawing Figure

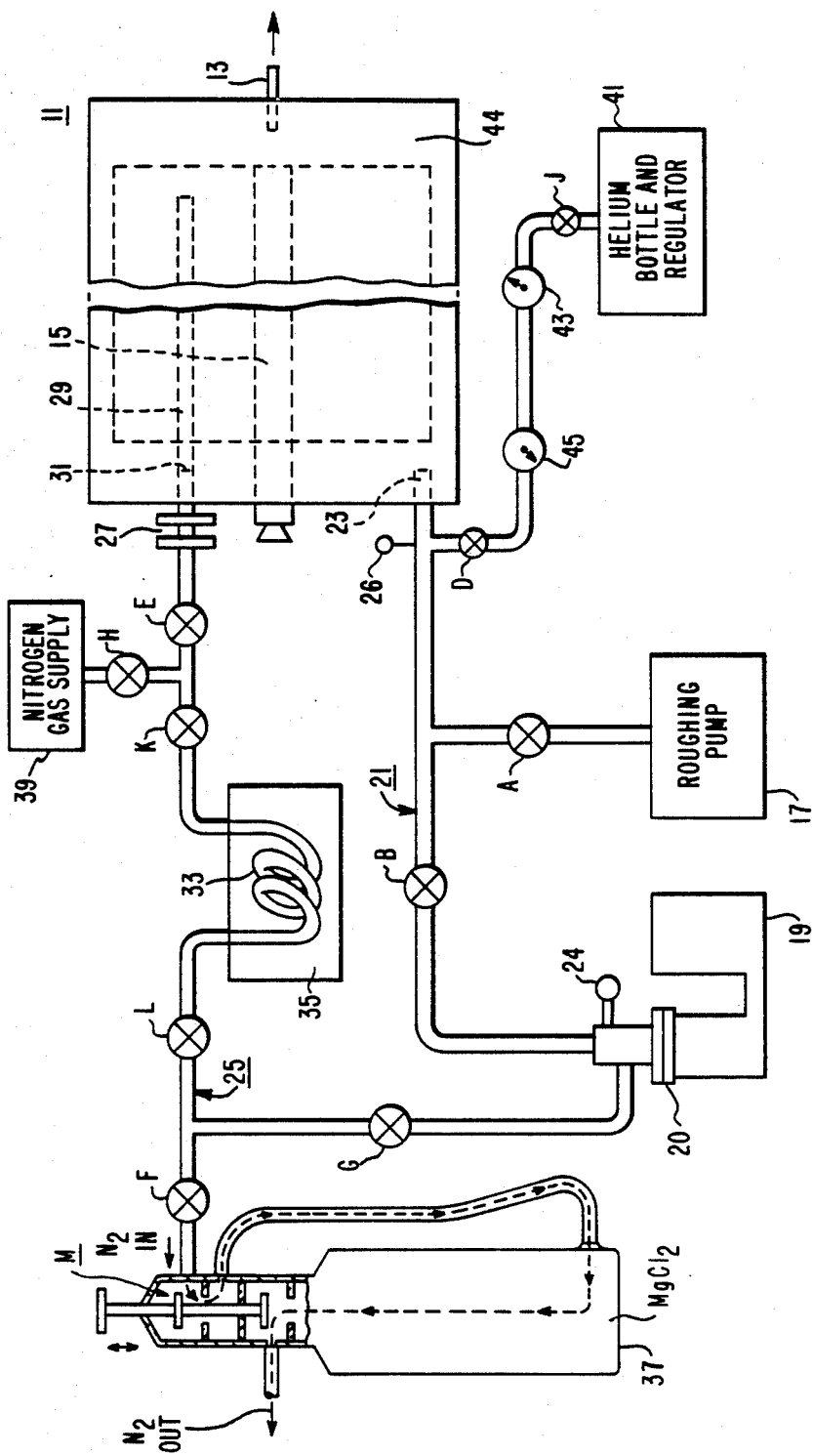

MEASUREMENT OF MOISTURE CONTENT

BACKGROUND OF THE INVENTION

This invention relates to the nuclear power art and it has particular relationship to nuclear fuel rods. A nuclear fuel rod includes cladding of Zircaloy alloy or stainless steel within which there are stacked or otherwise disposed a plurality of nuclear fuel pellets, typically $UO_2$. A requirement which is imposed on such rods, particularly when they are used in boiling water reactors (BWRs), is that the moisture content within the rods be maintained at a minimum magnitude. Typically, in the case of rods which are about 12 feet in length, this limit is 6 milligrams although some specifications set the limit at 12 mg. The moisture content of the pellets which are inserted in the rods is known and the moisture content of a fuel rod as fabricated can be computed from the moisture-content data of the individual pellets. This moisture content exceeds that set limit and it is necessary to treat or process the rods in a drying oven at low pressure to reduce the moisture content to the required specification. Each rod has a perforation at one end, typically about 0.030 inch in diameter, through which moisture escapes during the treatment. For determination of the residual moisture content following or during the treatment, it is necessary that the mass of the moisture removed from each rod be determined. The residual moisture content is determined by subtracting the determined weight of the moisture from the computed magnitude based on the moisture content in the pellets in each rod.

Prior to this invention, no convenient or practicable method or apparatus was available for determining the moisture content in each of a plurality, usually a large number of fuel rods. It is an object of this invention to determine reliably the moisture content in each of a plurality of nuclear fuel rods during or after treatment in a drying oven. More specifically, it is an object of this invention to provide an on-line method and apparatus for carrying out this determination; i.e., a method and apparatus which can be used, while the rods are being processed, without removing the rods from the oven.

SUMMARY OF THE INVENTION

The fuel rods are treated in an oven, which is evacuated, typically to 5 to 20 microns, and at 200° C. to 250° C., for a predetermined time interval. The length of the interval depends on the structure of the oven. In a typical situation, the duration of the interval is about 6 hours. In accordance with this invention, the moisture vapor emitted from one fuel rod, selected at random, is removed through a channel, which is at the same pressure as exists in the oven, and is condensed. Several randomly-selected fuel rods can also serve for this sampling process. The weight of the condensed moisture is then determined. The difference between the computed weight and the determined weight is the residual weight of moisture in the one fuel rod. During the processing, the moisture in the one rod is collected and has its weight determined repeatedly in repeated increments. Each increment is weighed and when the weight of a last increment is less than the weight of a just proceeding increment by a predetermined low magnitude (typically $\leq 1$ mg.), the processing is completed. Since the one rod is treated at the same pressure and at the same temperature as the other rods, the residual vapor in the other rods is equal to the residual vapor in the one rod. This equality has been verified by extensive comparison measurements of the moisture in the other rods separately. If the measured residual moisture in the one rod is greater than the specification, the treating cycle for all rods is repeated until the specification is achieved.

The apparatus according to this invention includes the oven and an evacuating system for the oven which has, in addition to the main channel directly connected to the oven, a branch or auxiliary channel that is connected to the one fuel rod in the oven through a cold trap. Valves are provided for isolating the cold trap from the evacuating system and for isolating the trap from the one fuel rod. The trap is connected to a moisture collector through another valve and to a supply of nitrogen through still another valve. The trap is cooled by liquified gas, typically liquid nitrogen. The repeated cycling is carried out to assure that the moisture caught by the cold trap has been completely removed and accounted for.

In the practice of the method according to this invention, the temperature of the oven is raised to the desired magnitude and the evacuating system is enabled, evacuating the oven through the main channel and the one fuel rod through the branch channel to the same pressure. At this time, the valve between the cold trap and the collector is closed. The air and moisture in the one fuel rod is evacuated through the branch channel and the cold trap. The cold trap is maintained in liquid nitrogen so that it condenses the moisture. After the oven has been evacuated to the required pressure and has been maintained at the required pressure and temperature for the required interval, the cold trap is isolated by closing valves between the cold trap and the oven and between the cold trap and the evacuating pumps. The liquified gas is removed from the cold trap, the valve between the cold trap and the moisture collector is opened and a stream of a non-reactive gas such as nitrogen is passed through the cold trap so that the condensed moisture in the cold trap is evaporated and driven into the collector. The weight of the collected vapor may then be determined. As stated, the moisture is processed through the cold trap and the collector in repeated increments which are weighed and whose weights are compared.

BRIEF DESCRIPTION OF THE DRAWING

For a better understanding of this invention, both as to its organization and as to its method of operation, together with additional objects and advantages thereof, reference is made to the following description, taken in conjunction with the accompanying drawing, in which the single FIGURE is a diagrammatic view of apparatus in accordance with this invention used in the practice of the method in accordance with this invention.

DETAILED DESCRIPTION OF THE INVENTION

The apparatus shown in the drawing includes an electrically heated drying oven 11 for drying the nuclear fuel rods. A typical oven has the capacity for treating or processing about 44 fuel rods. The oven is pressure tight so that it is capable of holding a vacuum. It has a pressure safety valve 13 for relieving pressure. The oven is heated by heating coils (not shown) which are divided into a number of separately heated zones (not shown) extending axially along the oven. Typically, there are six zones; they are numbered 1 through 6 from the left-hand end of the oven (as seen in the drawing) to the right-hand end. Thermocouples 15 are disposed in the oven 11 for determining its temperature.

For evacuating the oven the apparatus includes a roughing pump 17, a vane pump or molecular pump 19, and a turbo pump 20. There is also a main evacuating channel 21 which has a port 23 extending into the oven. A vacuum probe or transducer 24 is interposed between the turbo pump 20 and channel 21. There is also a vacuum probe or transducer 26 in channel 21 near port 23. In addition, there is an auxiliary or branch channel 25. A valve A is interposed between the roughing pump 17 and the main channel 21. A valve B is interposed in the channel 21 between the vane pump 19 and the port 23. The branch channel 25 includes a vacuum coupling 27 for connection to one of the fuel rods 29 as a sample rod. If it is desirable, there may be additional couplings or additional branch channels for connection to several sample fuel rods. The rod 29 is connected with its opening 31 in communication with the branch channel 25 so that the moisture in the rod can escape into the branch channel. The branch channel 25 includes a cold trap 33. Valves K and L are interposed, in the branch channel 25, on both sides of the cold trap so that the cold trap 33 can be removed from the branch channel without disturbing the other parts of the branch channel.

The cold trap 33 is immersed in a liquid nitrogen dewar 35. Through the branch channel 25 the fuel rod 29 is exhausted through the cold trap 33. A valve E is interposed in the branch channel between the rod 29 and the cold trap 33. A valve G is interposed between the pump 19 and the cold trap 33. At the end remote from the tube 29, the branch channel 25 is connected through valve F to a moisture collector 37, typically a bottle containing magnesium perchlorate. Between the rod 29 and the cold trap 33 the branch channel 25 is connected to a supply of nitrogen gas 39 through a valve H.

After the weight of the moisture for rod 29 is determined and found to be satisfactory, the oven 11 is backfilled with helium and then permitted to cool so that the rods can be removed. For this purpose a source 41 of helium is connected to the port 23 through a valve J, a pressure gage 43, a vacuum gage 45 and a valve D. Typically, the valves A through L are manually operable although the use of remotely controlled solenoid valves is within the scope of equivalents of this invention.

In the practice of this invention, the cold trap 33 is connected into channel 25 and valves K and L are opened. The following procedure is then carried out.

1. It is verified that the oven 11 is vented. The loading door of the oven is opened, the fuel rod 29 is placed in its location and the other fuel rods (not shown) are placed in their locations.

2. The end of fuel rod 29 which has the opening 31 is connected to the vacuum coupling 27 and valve E is closed.

3. The vacuum transducer 26 is connected so that transducer 26 monitors the vacuum in the oven 11.

4. Valves A, B, D, F, G, H, J are closed and E remains closed. Valves K and L are open. Since E, F, G and H are closed, the setting of K and L has no effect.

5. Roughing pump 17 is enabled and valve A is opened.

6. The dewar 35 is filled with liquid nitrogen.

7. The turbo pump 20 and the vane pump 19 are started and valves B and G are opened. The turbo pump and the vane pump operate together as a unit. After a certain vacuum is produced by the vane pump, the turbo pump goes into operation.

8. Valve H is opened part way for a short time, typically 1 minute, to flush the cold trap 33 with nitrogen.

9. Valve H is closed and then valve G is closed.

10. When the vacuum in oven 11 reaches, typically, 160 microns, the oven heaters are turned on.

11. Transducer 26 is disconnected and transducer 24 is connected and valve E is opened.

12. Valve G is opened slowly while vacuum gage (transducer 24) is monitored. The opening of valve G is continued, while the vacuum measured by transducer 24, is maintained between 100 and 150 microns, until valve G is completely opened.

13. Valve A remains open and valve B is closed. Transducer 24 is disconnected and transducer 26 is connected.

14. Roughing pump 17 is turned off. At this point, the oven vacuum should drop rapidly to about 25 microns.

15. The oven temperature is monitored.

16. When temperature zones 2 and 5 (not shown) reach 150°–175° C., they are turned off. When temperature zones 3 and 4 reach 200° C., all zones are turned off. The oven 11 is well insulated so that the temperature in the oven will be maintained or will increase slowly for about 2 hours.

17. Valves K and L on both sides of the cold trap 33 are closed. Then valves G and E are closed.

18. Liquid nitrogen dewar is removed.

19. Collector 37 is connected to the branch channel 25 and the valve M on the collector is opened for purging. In the drawing, valve M is shown in the open position. The gas which flows through the collector flows through the magnesium perchlorate before passing through the open valve on the collector.

20. Valve H is opened and valves K and L are opened and valve F is opened part way so that the flow of nitrogen through valve F and downstream from valve F in channel 25 has a predetermined magnitude, typically 40 cc/min.

21. The moisture is collected in collector 37 typically for 1 hour then valve F is closed. The collector valve M is closed and the collector is weighed.

22. The collector 37 is reconnected as described in paragraphs 19 and 20 and the moisture is collected in the magnesium perchlorate for ½ hour. Then collector 37 is removed and weighed again. The ½ hour moisture collection and weighing is repeated until the weight difference between a preceding weighing and the last weighing is $\leq 1$ mg.

The weight of the moisture removed is the sum of the weights of the increments removed. This sum is compared to the computed weight of the moisture. If the residual moisture is greater than the required quantity, i.e., 6 mg., the above cycle is repeated. In the practice of this invention, no incident has been experienced in which the above-described measurement required repetition of the cycle.

It is now necessary to go through the following cooling process so that the rods can be removed.

23. Valve B remains closed and the turbo pump 20 and vane pump 19 are turned off.

24. The helium bottle 41 is opened and the pressure gage 43 is set at about 0.25 psi.

25. Valve J is opened and then valve D is opened. As the helium leaks in, the pressure in the oven 11 is adjusted to about 1 inch of mercury.

26. The oven 11 is permitted to remain in the state set by step 25 for about 12 to 14 hours.

27. If, after this interval, the temperature is still above 100° C., valve J is closed, the roughing pump 17 is started and valve A is checked to determine if it is open and if not, it should be opened.

28. The roughing pump is operated until the vacuum in the oven is about 100 microns. Valve A is closed and the roughing pump 17 is turned off.

29. Valve J is now opened until a pressure of 1 inch of mercury is reached in the oven 11. The temperature is checked. This step and step 28 constitutes a flushing procedure and these steps are repeated until the temperature in the oven is ≦100° C.

30. After the temperature of the oven is equal to or less than 100° C., the oven is opened, the time is noted, the fuel rods are removed and temporarily capped as soon as practicable.

31. The rods are transferred several, for example, five at a time, in a channel to a pressure-seal welder where rods are pressurized to the desired level, then the openings 31 are sealed.

While a preferred embodiment and preferred practice of this invention are disclosed herein, many modifications thereof are feasible. This invention is not to be restricted except insofar as is necessitated by the spirit of the prior art.

We claim:

1. A method of determining moisture content within each of a plurality of nuclear fuel rods, each fuel rod including cladding containing therein a plurality of fuel pellets, the cladding of each fuel rod having an opening for escape of air and vapor of moisture from the interior thereof; said method being practiced with apparatus including a drying oven, evacuating means connected to said oven and to at-least one fuel rod randomly selected from said plurality of fuel rods, for evacuating said oven and said at-least one rod, and moisture-vapor condensing means connected to said at-least one rod through said evacuating means; said method including heating said fuel rods in said oven to a predetermined temperature for a predetermined interval of time, while said rods are being heated enabling said evacuating means to evacuate said oven and said at-least one rod, collecting said vapor of moisture from said at least one rod, through said evacuating means, in said moisture-vapor condensing means, condensing said vapor from said at-least one rod in said condensing means, thereafter evaporating said moisture from said at-least one rod condensed in said condensing means, and measuring the quantity of moisture which was condensed from said at-least one rod; the interior of said at-least one rod being maintained through its said opening by said evacuating means and said oven at the same pressure as the interior of the remaining plurality of fuel rods are maintained through their respective openings, whereby the measurement of the moisture within said at-least one rod is used as an equivalent measurement of the moisture within each of the remaining plurality of fuel rods.

2. The method of claim 1 wherein after the predetermined time interval during which the oven is heated, the moisture in the at-least one rod which was condensed in said condensing means is repeatedly, in repeated increments, collected and weighed and the total weight of the moisture in said at-least one rod is determined after an absolute difference between the weight of a last said increment and the weight of said increment just preceding said last said increment is less than a predetermined magnitude.

3. A method of determining moisture content within each of a plurality of nuclear fuel rods, each fuel rod including cladding containing therein a plurality of fuel pellets, the cladding of each fuel rod having an opening for escape of vapor of moisture from the interior thereof said method being practiced with apparatus including a drying oven, evacuating means connected to said oven and to at-least one fuel rod randomly selected from said plurality of fuel rods and moisture-vapor condensing means connected to said at-least one rod through said evacuating means; said method including heating said fuel rods in said oven at a predetermined temperature for a predetermined time interval, while said rods are being so heated enabling said evacuating means to evacuate said oven and said at-least one rod, while said at-least one rod is being so evacuated conducting the vapor of moisture within said at least one rod through said vapor condensing means so as to condense the moisture which was within said at-least one rod in said condensing means, and measuring the quantity of said condensed moisture; the interior of said at-least one rod being maintained through its said opening by said evacuating means and said oven at the same pressure and temperature as the interior of the remaining plurality of fuel rods are maintained through their respective openings, whereby the measurement of the quantity of moisture within said at-least one rod is used as an equivalent measurement of the quantity of moisture within each of the remaining plurality of fuel rods.

4. The method of claim 3 wherein the apparatus for practicing the method includes measuring means having means for absorbing vapor and said method includes the following steps carried out after the end of the time interval during which the oven is heated;

a. conducting the moisture content of the condensing means to the absorbing means to be absorbed thereby, and b. measuring the quantity of moisture absorbed in the absorbing means.

5. The method of claim 4 wherein the moisture in the condensing means is driven into the absorbing means by a stream of a non-reactive gas.

6. The method of claim 3 wherein after the predetermined time interval, the moisture in the at-least one fuel rod which was condensed in said condensing means is repeatedly, in repeated increments, collected and weighed and the total weight of the moisture in said at-least one fuel rod is determined after an absolute difference between the weight of a last said increment and the weight of said increment just preceding said last said increment is less than a predetermined magnitude.

7. The method of claim 3 wherein the apparatus for practicing the method includes measuring means having means for absorbing vapor and said method includes repetition a number of times of the following steps carried out after the time interval during which the oven is heated;

a. conducting said condensed moisture of the condensing means to the absorbing means to be absorbed thereby, b. measuring the quantity of said moisture absorbed in the absorbing means, and c. comparing the moisture measurement obtained during each set of steps (a) and (b) with the moisture measurement for the just preceding set of steps (a) and (b), after the comparison shows a decrease less than a predetermined magnitude terminating said repetition, and after said termination adding the moisture measurements determined by repeated step (b) as a measure of the moisture content of each of the plurality of fuel rods.

8. Apparatus for determining moisture content within each of a plurality of nuclear fuel rods, each fuel rod including cladding containing therein a plurality of fuel pellets, the cladding of each fuel rod having an opening for emission of vapor of moisture from the interior thereof; said apparatus including a drying oven wherein said plurality of rods is to be disposed for processing, evacuating means, means connecting said evacuating means to said oven to evacuate said oven, said evacuating means including a branch evacuating channel, moisture condensing means, means connected to said branch channel for connecting said branch channel to at least one full rod randomly selected from said plurality of fuel rods through said condensing means, and moisture measuring means connected to said condensing means for measuring condensed moisture therein; the interior of the remaining plurality of fuel rods being maintained by evacuation through its said opening by said evacuating means at the same pressure as the interior of said at-least one rod is maintained by evacuation through its said opening, whereby the measurement of said condensed moisture by said measuring means is used as an equivalent measurement of the moisture within each of the remaining plurality of fuel rods.

9. The apparatus of claim 8 wherein the condensing means includes a cold trap to be interposed between the evacuating means and the at least one fuel rod, and the measuring means includes means connected to the cold trap for absorbing the condensed moisture condensed in said cold trap.

10. The apparatus of claim 9 including first valve means interposed between the evacuating means and the cold trap, second valve means to be interposed between the at least one fuel rod and the condensing means, and third valve means interposed between the cold trap and the measuring means.

11. The apparatus of claim 9 including means to be connected to the cold trap for supplying a gas stream to drive the condensed moisture therein into the measuring means.

12. The apparatus of claim 11 including valve means to be interposed in the gas supply means.

* * * * *